United States Patent [19]

Nedelec et al.

[11] 4,313,944
[45] Feb. 2, 1982

[54] CYCLOHEPTINDOLES, COMPOSITIONS AND USE

[75] Inventors: Lucien Nedelec, Le Raincy; Daniel Frechet, Paris; Claude Dumont, Nogent sur Marne, all of France

[73] Assignee: Roussel Uclaf, Paris, France

[21] Appl. No.: 237,062

[22] Filed: Feb. 23, 1981

[30] Foreign Application Priority Data

Feb. 26, 1980 [FR] France .................. 80 04198

[51] Int. Cl.³ .................. A61K 31/535; C07D 498/04
[52] U.S. Cl. .................. 424/248.4; 424/248.52; 424/248.58; 544/99
[58] Field of Search .......... 544/99; 424/248.4, 248.52, 424/248.58

[56] References Cited
U.S. PATENT DOCUMENTS 4,238,486 12/1980 Jones .................. 544/99

Primary Examiner—John M. Ford
Assistant Examiner—R. W. Ramsuer
Attorney, Agent, or Firm—Hammond & Littell, Weissenberger and Muserlian

[57] ABSTRACT

Novel compounds selected from the group consisting of optically active isomers and racemic mixtures of cycloheptindoles of the formula

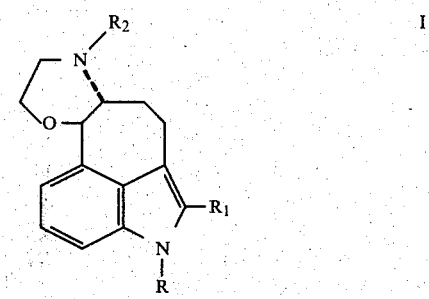

wherein R is selected from the group consisting of hydrogen, alkyl of 1 to 5 carbon atoms and optionally substituted aralkyl of 7 to 12 carbon atoms, $R_1$ is selected from the group consisting of hydrogen, chlorine and bromine and $R_2$ is selected from the group consisting of hydrogen, alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and their non-toxic, pharmaceutically acceptable acid addition salts having dopaminergic agonist and antianoxic properties and a process for their preparation and novel intermediates.

18 Claims, No Drawings

CYCLOHEPTINDOLES, COMPOSITIONS AND USE

OBJECTS OF THE INVENTION

It is an object of the invention to provide the novel cycloheptindoles of formula I and their non-toxic, pharmaceutically acceptable acid addition salts and a novel process and novel intermediates for their preparation.

It is another object of the invention to provide novel composition having antianoxic and dopaminergic agonist activity and to a novel method of inducing antianoxic and dopaminergic agonist activity in warm-blooded animals.

These and other objects and advantages of the invention will become obvious from the following detailed description.

THE INVENTION

The novel compounds of the invention are selected from the group consisting of optically active isomers and racemic mixtures of cyclohept indoles of the formula

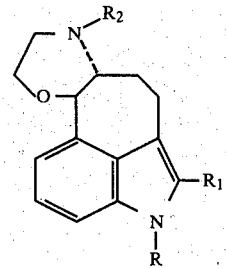

wherein R is selected from the group consisting of hydrogen, alkyl of 1 to 5 carbon atoms and optionally substituted aralkyl of 7 to 12 carbon atoms, $R_1$ is selected from the group consisting of hydrogen, chlorine and bromine and $R_2$ is selected from the group consisting of hydrogen, alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and their non-toxic, pharmaceutically acceptable acid addition salts.

Examples of alkyl of 1 to 5 carbon atoms of formula I are methyl, ethyl, propyl, isopropyl, butyl, isobutyl and pentyl and examples of optionally substituted aralkyl of 7 to 12 carbon atoms are benzyl and phenethyl substituted with at least one member of the group consisting of chlorine, bromine, methyl, ethyl, methoxy, methylthio and trifluoromethyl. Examples of cycloalkylalkyl of 4 to 7 carbon atoms are cyclopropylmethyl and examples of alkenyl and alkynyl of 3 to 7 carbon atoms are allyl, buten-2-yl and propargyl.

Examples of suitable acids to form the non-toxic, pharmaceutically acceptable acid addition salts are mineral acids such as hydrochloric acid, hydrobromic acid, nitric acid, sulfuric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, arylsulfonic acids such as benzene sulfonic acid and p-toluene sulfonic acid and arylcarboxylic acids. The dotted line at the junction of the morpholino ring and the cycloheptene ring is trans.

Among the preferred compounds of formula I of the invention are those wherein R is hydrogen, methyl or benzyl, those wherein $R_2$ is hydrogen, alkyl of 1 to 5 carbon atoms or cycloalkylalkyl of 4 to 7 carbon atoms and their non-toxic, pharmaceutically acceptable acid addition salts. Especially preferred are the compounds of formula I wherein R is hydrogen, $R_1$ is hydrogen or bromine and $R_2$ is hydrogen or alkyl of 1 to 5 carbon atoms and their acid addition salts.

The novel process of the invention for the preparation of the compounds of formula I comprises reacting a compound of the formula

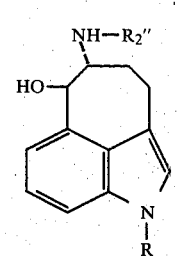

wherein R has the above definition and $R''_2$ is selected from the group consisting of hydrogen, alkyl of 1 to 5 carbon atoms, cycloalkylalkyl of 4 to 7 carbon atoms and optionally substituted aralkyl of 7 to 12 carbon atoms with chloroacetyl chloride to obtain a compound of the formula

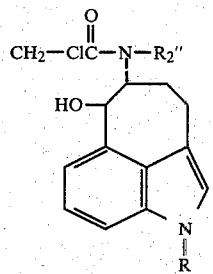

cyclizing the latter to obtain a compound of the formula

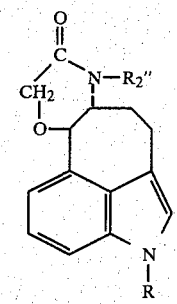

reducing the latter to obtain a compound of the formula

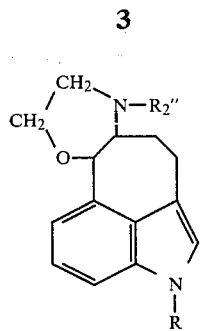

I_A which is a compound of formula I wherein $R_2$ is $R''_2$ and $R_1$ is hydrogen and either optionally, if desired, salifying the latter or treating a compound of formula $I_A$ with a halogenation agent to obtain a compound of the formula

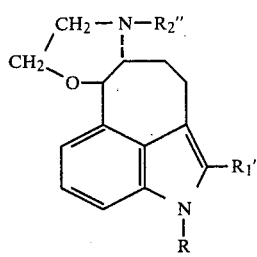

I_B wherein $R'_1$ is selected from the group consisting of chlorine and bromine which is a compound of formula I wherein $R_1$ is $R'_1$ and $R_2$ is $R''_2$ which may be optionally salified or when $R''_2$ is hydrogen reacting a compound of formula $I_A$ with a halide of formula Hal-$R'_2$ V wherein Hal is chlorine, bromine or iodine and $R'_2$ has the definition of $R_2$ except for hydrogen to obtain a compound of the formula

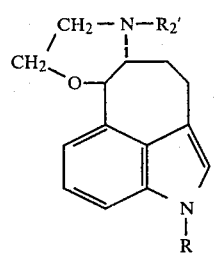

I_C which is a compound of formula I wherein $R_1$ is hydrogen and $R_2$ is $R'_2$ which may be optionally salified or a compound of formula $I_C$ is reacted with a halogenation agent to obtain a compound of the formula

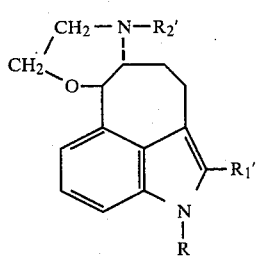

I_D which is a compound of formula I wherein $R_1$ is $R'_1$ and $R_2$ is $R'_2$ which may be optionally salified or when $R''_2$ is hydrogen reacting a compound of formula $I_A$ with a formylation agent to obtain a compound of the formula

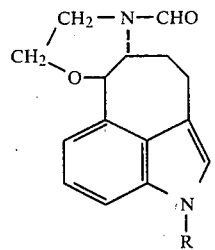

VI and reducing the latter to obtain a compound of the formula

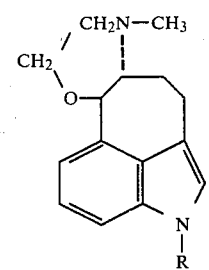

I_E which is a compound of formula I wherein $R_1$ is hydrogen and $R_2$ is methyl which may optionally be salified or reacting a compound of formula $I_E$ with a halogenation agent to obtain a a compound of the formula

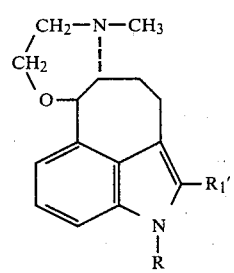

I_F which is a compound of formula I wherein $R_1$ is $R'_1$ and $R_2$ is methyl which may optionally be salified or when R is hydrogen and $R''_2$ has the definition as above except for hydrogen reacting a compound of formula $I_A$ with a halide of the formula Hal-R' VII when R' is R other than hydrogen and Hal is as defined above to obtain a compound of the formula

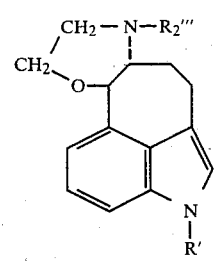

I_G wherein $R'''_2$ is $R''_2$ other than hydrogen which is a compound of formula I wherein R is R' and $R_2$ is $R'''_2$ which may optionally be salified or reacting a compound of formula $I_G$ with a halogenation agent to obtain a compound of the formula

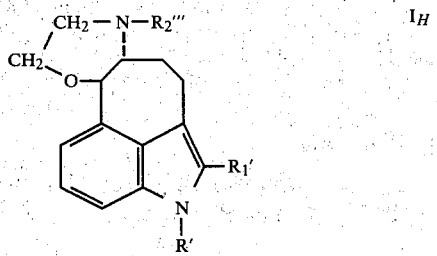

which is a compound of formula I wherein R is R′, $R_1$ is $R'_1$ and $R_2$ is $R'''_2$ which may be optionally salified.

In a preferred mode of the process of the invention, the condensation of the compound of formula II with chloroacetyl chloride is effected in the presence of an acid fixation agent such as sodium hydroxide in an organic solvent such as dioxane or tetrahydrofuran but preferably tetrahydrofuran in the presence of water. The cyclization of the compound of formula III is preferably effected with sodium hydride but equally useful are other bases such as sodium hydroxide or potassium hydroxide and the reaction is effected in dimethylformamide or dimethoxy ethane. The reduction of the compound of formula IV is effected preferably with lithium aluminum hydride in a solvent such as dioxane or preferably tetrahydrofuran.

The halogenation agents are, for example, N-chlorosuccinimide for chlorination or N-bromo-succinimide or preferably a bromine complex of 2-pyrrolidone of the formula

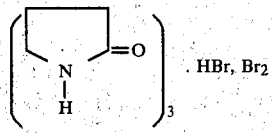

for bromination. The halide of formula V is preferably the iodide and its reaction with the secondary amine of formula $I_4$ is effected in the presence of acid acceptor such as an alkali metal carbonate like potassium carbonate in a solvent such as dimethylformamide. The formylation may be effected with formic acid but the preferred agent is formylacetic anhydride using a solvent such as tetrahydrofuran. The halide of formula VII is preferably the iodide and the reaction is effected in a strongly basic medium such as in the presence of sodium amide.

The racemates of formula I may be resolved into their optically active enantiomers by known methods such as formation of salts with optically active acids. Since the compounds of formula I have a basic character, the acid addition salts may be formed by reaction with stoichiometric amounts of an acid.

The novel antianoxic and dopaminergic agonist compositions of the invention are comprised of an antianoxically and dopaminergic agonistically effective amount of at least one compound of formula I and their non-toxic, pharmaceutically acceptable acid addition salts and an inert pharmaceutical carrier. The compositions may be in the form of tablets, dragees, gelules, granules, suppositories and injectable solutions or suspensions.

Certain of the compositions also possess antiulcerogenic activity.

Examples of suitable pharmaceutical carriers are talc, arabic gum, lactose, starch, magnesium stearate, cacao butter, fatty bodies of animal or vegetable origin, aqueous and non-aqueous vehicles, paraffinic derivatives, glycols, diverse wetting agents, dispersants or emulsifiers and preservatives.

The compositions are useful for the treatment of neurological syndromes of extra pyramidal origin such as for the treatment of Parkinson disease and the treatment of post-encephalitic Parkinson syndromes. They are also useful for the treatment of prolactin hypersecretion by antehypophysis such as for the treatment of hypogonadism in the male or female. They are also useful for the treatment of cerebral senescence or manifestation of a cerebral, hypoxia. Certain compositions are useful for treatment of hyperchlorhydria, of gastric ulcers and gastroduodenal affections accompanying gastric hyperacidity.

Among the preferred compositions of the invention are those containing as the active ingredient compounds of formula I wherein R is hydrogen methyl or benzyl, those wherein $R_2$ is hydrogen, alkyl of 1 to 5 carbon atoms or cycloalkylalkyl of 4 to 7 carbon atoms and their non-toxic, pharmaceutically acceptable acid addition salts. Especially, preferred are the compounds of formula I wherein R is hydrogen, $R_1$ is hydrogen or bromine and $R_2$ is hydrogen or alkyl of 1 to 5 carbon atoms and their pharmaceutically acceptable acid addition salts.

The novel method of the invention of inducing antianoxic and dopaminergic agonist activity in warm-blooded animals, including humans, comprises administering to animals an amount of at least one compound of formula I and their non-toxic, pharmaceutically acceptable acid addition salts sufficient to cause antianoxic and dopaminergic agonist activity. The compounds may be administered orally, rectally or parenterally and the usual daily dose will vary depending on the condition being treated, the specific compound and the method of administration. The usual daily oral dose is 0.1 to 2 mg/kg of the compound of Example 3 for the treatment of Parkinson disease.

The compounds of formula II are novel and when $R''_2$ is alkyl of 1 to 5 carbon atoms, cycloalkylalkyl of 4 to 7 carbon atoms or optionally substituted aralkyl of 7 to 12 carbon atoms, are prepared by reacting a compound of formula II wherein $R''_2$ is hydrogen with trifluoroacetic acid anhydride preferably in the presence of a base to obtain a compound of the formula

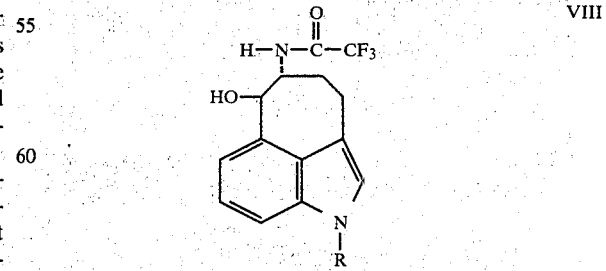

and reacting the latter in the presence of a base such as an alkali metal carbonate or alkali metal hydroxide or a tertiary amine with a halide of formula Hal-$R''_2$ IX wherein Hal and R''₂ have the above definition to obtain a compound of the formula

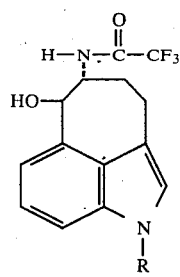

which is then reacted with an agent able to hydrolyze the trifluoroacetamide group to obtain the compounds of formula II.

In a preferred method of preparing the compounds of formula II wherein R''₂ is methyl, an alkyl carbamate, preferably ethyl may be prepared, on a non-indolic nitrogen atom, then the said carbamate is reduced. The carbamate may be prepared by reaction of a compound of formula II wherein R''₂ is hydrogen with an alkyl haloformate in the presence of a base such as an alkali metal carbonate. The reduction may be effected with lithium aluminium hydride in refluxing tetrahydrofuran.

To prepare the compound of formula II wherein R''₂ is ethyl, the N-acetyl derivative is formed and then is reduced. To prepare the compound of formula II wherein R''₂ is isopropyl, a compound of formula II wherein R''₂ is hydrogen is reacted with acetone in the presence of a reducing agent such as sodium cyanoborohydride.

The compounds of formula II wherein R and R''₂ are hydrogen may be prepared by reacting 3,4-dihydro-1H-cyclohept [c,d]indol-6-one [Chem. Pharm. Bull., Vol. 25 (11) (1977), p. 3023] with tert.-butyl nitrite in the presence of hydrochloric acid and reducing the resulting keto-oxime such as by hydrogenation, and then reacting with sodium borohydride.

The compounds of formula II wherein R''₂ is hydrogen may be prepared by reacting a compound of the formula Hal-R wherein R and Hal have the above definition except R is other than hydrogen with 3,4-dihydro-1H-cyclohept[c,d]indol-6-one by the phase transfer of Bosco et al [Synthesis, Vol. 2 (1976), p. 124], for example, in the presence of a quaternary ammonium salt such as tetra-butylammonium chloride or benzyltriphenyl phosphonium chloride or preferably tetrabutyl ammonium acid sulfate, aqueous sodium hydroxide and benzene, then preparing the oxime thereof and reducing the same.

In the following examples there are described several preferred embodiments to illustrate the invention. However, it should be understood that the invention is not intended to be limited to the specific embodiments.

EXAMPLE 1

(7a R,S-trans)-4,6,7,7a,8,9,10,11a-octahydro-[1,4]-oxazino [2',3'-4,5]-cyclohept[1,2,3-c,d]-indole hydrochloride STEP A: 5-oxime of 3,4-dihydro-1H-cyclohept[c,d]indol-5,6-dione 22 ml of 5 N hydrochloric acid in ethanol were added under nitrogen to a stirred solution of 18.5 g of 3,4-dihydro-1H-cyclohept[c,d]indol-6-one [Chem. Pharm. Bull., Vol. 25 (11) (1977), page 3023] in 185 ml of tetrahydrofuran cooled in an ice bath and then 13.5 ml of tert.-butyl nitrite were added thereto. The mixture was stirred in the ice bath for 30 minutes and was then vacuum filtered and the recovered product was washed with ether and dried under reduced pressure at 80° C. to obtain 19.4 g of 5-oxime of 3,4-dihydro-1H-cyclohept[c,d]indole-5,6-dione melting at 235° C. with decomposition.

STEP B: 5-R,S-trans amino 3,4,5,6-tetrahydro-1H-cyclohept[c,d]indole-6-ol and its acetate 2.5 g of 10% palladized activated carbon were added to a suspension of 5 g of the product of Step A in 100 ml of methanol and the mixture was stirred under hydrogen at room temperature for 40 minutes and was then vacuum filtered. The filtrate was cooled in an ice bath and 2.5 g of sodium borohydride were added thereto over 10 minutes and the mixture was stirred at room temperature under an inert atmosphere. The mixture was evaporated to dryness and the residue was taken up in refluxing methylene chloride. The mixture was filtered and the filtrate was evaporated to dryness. The residue was dissolved in 7 ml of methanol at 50° C. and 70 ml of ethyl acetate were added to the mixture which was then filtered. The filter was rinsed with ethyl acetate and the filtrate was concentrated to 50 ml and 25 ml of 1.1 N acetic acid in ethyl acetate were added thereto. The mixture stood at room temperature for one hour, was iced for 30 minutes and vacuum filtered and the product was dried under reduced pressure at 70° C. to obtain 4.9 g of the acetate of 5-R,S-trans amino 3,4,5,6-tetrahydro-1H-cyclohept[c,d]indol-6-ol melting at 150° C. After crystallization from a 1-1 methanol-ethyl acetate mixture, the acetate occured in the form of white crystals melting at 165° C.

Analysis: C₁₂H₁₄N₂O. C₂H₄O₂; molecular weight=262.30. Calculated: %C, 64.10; %H, 6.92; %N, 10.68. Found: %C, 64.2; %H 7.1; %N, 10.4.

10.8 g of the said acetate were suspended in 300 ml of ethyl acetate and 100 ml of concentrated ammonium hydroxide were added thereto with stirring. The mixture was saturated with sodium chloride and the mixture was stirred under nitrogen for 15 minutes. The decanted organic phase was washed with aqueous sodium chloride, was dried and evaporated to dryness to obtain 9.8 g of 5-R,S-trans amino-3,4,5,6-tetrahydro-1H-cyclohept[c,d]indol-6-ol.

STEP C: (5-R,S-trans) 2-chloro-N-(6-hydroxy-3,4,5,6-tetrahydro-1H-cyclohept[c,d]indol-5-yl)-acetamide A solution of 9.8 g of R,S-trans 5-amino-3,4,5,6-tetrahydro-1H-cyclohept[c,d]indol-6-ol and 100 ml of tetrahydrofuran was added under an inert atmosphere to a solution of 2.47 g of sodium hydroxide in 25 ml of water and then 3.65 ml of chloroacetyl chloride were added to the mixture with stirring over 15 minutes. The mixture was stirred for 45 minutes and the decanted organic phase was washed with aqueous sodium chloride. The mixture was extracted with ethyl acetate and the organic phase was dried and evaporated to dryness to obtain 13 g of raw (5-R,S-trans) 2-chloro-N-(6-hydroxy-3,4,5,6-tetrahydro-1H-cyclohept[c,d]indol-5-yl)-acetamide.

STEP D: (7a-R,S-trans) 4,6,7,7a,10,11a-hexahydro-[1,4]oxazino[2',3'-4,5]-cyclohept-[1,2,3,-c,d]-indol-9(8H)-one 2.17 g of sodium hydride as a 50% oil suspension were washed with petroleum ether (b.p.=60°-80° C.) and 10 ml of dimethylformamide were added thereto. A solution of the product of Step C in 50 ml of dimethylformamide were added over 15 minutes under an inert atmosphere to the mixture which was stirred for 80 minutes and was iced. 250 ml of water were added to the mixture which was stirred for 30 minutes and was vacuum filtered. The product was washed with water and dried at 80° C. under reduced pressure to obtain 9 g of (7a R,S-trans) 4,6,7,7a,10,11a-hexahydro-[1,4]oxazino [2',3'-4,5]-cyclohept-[1,2,3,-c,d]-indol-9(8H)-one as a beige solid melting at more than 280° C. with decomposition.

STEP E: (7a-R,S-trans)-4,6,7,7a,8,9,10,11a-octahydro-[1,4]-oxazino-[2',3'-4,5]cyclohept-[1,2,3-c,d]-indole hydrochloride 12.13 g of the product of Step D were added over 10 minutes under an inert atmosphere to a suspension of 6 g of lithium aluminum hydride in 400 ml of tetrahydrofuran and the mixture was refluxed for 3 hours after which another 6 g of lithium aluminum hydride were added thereto at 20° C. The mixture was refluxed for 3¼ hours and was rapidly cooled to 20° C. 300 ml of tetrahydrofuran containing 20% of water were added to the mixture which was stirred for 15 minutes and was filtered. The product was rinsed with 1000 ml of methylene chloride containing 10% of methanol and was dried to obtain 14 g of raw product. The latter was taken up in methylene chloride and the solution was washed with water, dried, treated with activated carbon and filtered. The filtrate was evaporated to dryness and the residue was chromatographed over silica gel. Elution with a 7-2-1 cyclohexane-ethanol-triethylamine mixture yielded 5.61 g of (7a-R,S-trans)-4,6,7,7a,8,9,10,-11a-octahydro-[1,4]-oxazino-[2',3'-4,5]cyclohept-[1,2,3-c,d]-indole in the form of a beige solid melting at 198° C. and then 204° C.

The said product was dissolved in 80 ml of methanol at 60° C. and an excess of a solution of hydrogen chloride in ethyl acetate was added thereto. The mixture was iced and vacuum filtered and the product was washed with ethyl acetate, dried and crystallized from methanol to obtain 6.1 g of (7a-R,S-trans)-4,6,7,7a,8,9,10,11a-octahydro-[1,4]-oxazino-[2',3'-4,5]cyclohept-[1,2,3-c,d]-indole hydrochloride in the form of a beige solid melting at greater than 280° C. with decomposition.

Analysis: $C_{14}H_{16}N_2O$. HCl; molecular weight=264.75. Calculated: %C, 63.52; %H, 6.47; %N, 10.58; %Cl, 13.39. Found: %C, 63.6; %H, 6.5; %N, 10.3; %Cl, 13.4.

EXAMPLE 2

(7a-R,S-trans) 8-methyl-4,6,7,7a,8,9,10,11a-octahydro-[1,4]-oxazino-[2',3'-4,5]cyclohept[1,2,3-c,d]indole hydrochloride

STEP A: (7a-R,S-trans) 4,6,7,7a,8,9,10,11a-octahydro-[1,4]-oxazino-[2',3'-4,5]cyclohept[1,2,3-c,d]indole-8-carboxaldehyde 1.9 ml of formyl acetic anhydride were added under an inert atmosphere to a suspension of 4.3 g of the free base of Example 1 in 86 ml of tetrahydrofuran and the mixture was stirred for 30 minutes and was vacuum filtered. The product was washed with ether and dried at 60° C. under reduced pressure to obtain 4.65 g of (7a-R,S-trans) 4,6,7,7a,8,9,10,11a-octa-hydro-[1,4]-oxazino-[2',3'-4,5]cyclohept[1,2,3-c,d]indole-8-carboxaldehyde in the form of a white solid melting towards 275° C.

STEP B: (7a-R,S-trans) 8-methyl-4,6,7,7a,8,9,10,11a-octa-hydro-[1,4]-oxazino-[2',3'-4,5]cyclohept[1,2,3-c,d]-indole hydrochloride The product of Step A was introduced over 10 minutes under an inert atmosphere at 6° to 8° C. to a suspension of 1.38 g of lithium aluminum hydride in 80 ml of tetrahydrofuran and the mixture was refluxed for 50 minutes and was cooled to 10° C. 30 ml of tetrahydrofuran containing 20% water were added at 10° C. to the mixture which was then filtered and the filtrate was washed with aqueous sodium chloride solution. The aqueous phase was extracted with ethyl acetate and the extract was dried and evaporated to dryness to obtain 4.2 g of a white solid melting at 170° C. which was (7a-R,S-trans)8-methyl-4,6,7,7a,8,9,10,11a-octahydro-[1,4]-oxazino-[2',3'-4,5]cyclophept[1,2,3-c,d]indole.

The 4.2 g of base were dissolved in 80 ml of ethyl acetate at 60° C. and an excess of hydrogen chloride in ethyl acetate was added thereto. The mixture was concentrated under an inert atmosphere at room temperature and was then iced and vacuum filtered. The product was washed with ethyl acetate, dried and crystallized from methanol to obtain 3.8 g of (7a-R,S-trans) 8-methyl-4,6,7,7a,8,9,10,11a-octahydro-[1,4]-oxazino-[2',3'-4,5]cyclohept[1,2,3-c,d]indole hydrochloride in the form of a white solid melting towards 270° C.

Analysis: $C_{15}H_{18}N_2O$. HCl; molecular weight=278.78. Calculated: %C, 64.63; %H, 6.87; %N, 10.05; %Cl, 12.72. Found: %C, 64.9; %H, 6.9; %N, 10.0; %Cl, 13.0.

EXAMPLE 3

(7a-R,S-trans)-4,6,7,7a,8,9,10,11a-octahydro-8-propyl-[1,4]-oxazino-[2',3'-4,5]cyclohept[1,2,3-c,d]indole hydrochloride A suspension of 5.34 g of the free base of Example 1, 8.46 g of potassium carbonate and 4.03 ml of 98% iodopropane was stirred under an inert atmosphere at 60° C. for 4 hours and was then cooled to room temperature. 300 ml of water were added to the mixture which was extracted with ethyl acetate. The organic phase was washed with water, dried and evaporated to dryness to obtain 5.5 g of (7a-R,S-trans) 4,6,7,7a,8,9,10,11a-octahydro-8-propyl-[1,4]-oxazino-[2',3'-4,5]cyclohept[1,2,3-c,d] indole melting at 170° C.

The said base was dissolved in 120 ml of ethyl acetate at 50° to 60° C. and a solution of 2 N hydrogen chloride in ethyl acetate was slowly added thereto with stirring. The mixture was stirred at 50° C. for crystallization and stood in the refrigerator for one hour and was vacuum filtered. The product was washed with ethyl acetate, dried at 60° C. under reduced pressure, treated with activated carbon and crystallized from methanol to obtain 4.35 g of (7a-R,S-trans)-4,6,7,7a,8,9,10,11a-octahydro-8-propyl-[1,4]-oxazino-[2',3'-4,5]cyclohept[1,2,3-c,d]indole hydrochloride in the form of a white solid melting towards 260° C. with decomposition.

Analysis: $C_{17}H_{22}N_2O$. HCl; molecular weight = 306.83. Calculated: %C, 66.55; %H, 7.55; %N, 9.13; %Cl, 11.55. Found: %C, 66.5; %H, 7.5; %N, 9.1; %Cl, 11.4.

EXAMPLE 4

(7a-R,S-trans) 5-bromo-4,6,7,7a,8,9,10,11a-octahydro-8-propyl-[1,4]-oxazino-[2',3'-4,5]cyclohept[1,2,3-c,d]indole hydrochloride A solution of 5 g of pyrrolidone trihydrobromide in 250 ml of methylene chloride was slowly added to a solution of 3 g of the free base of Example 3 in 100 ml of methylene chloride and the mixture was stirred at 20° C. for 30 minutes. 300 ml of aqueous saturated sodium bicarbonate solution were added to the mixture and the decanted organic phase was washed with water, dried and evaporated to dryness to obtain 4.1 g of residue. The latter was chromatographed over silica gel and was eluted with a 4-4-2 cyclohexane-chloroform-triethylamine mixture to obtain 2.6 g of (7a-R,S-trans) 5-bromo-4,6,7,7a,8,9,10,11a-octahydro-8-propyl-[1,4]-oxazino-[2',3'-4,5]cyclohept[1,2,3-c,d]indole.

The 2.6 g of product were dissolved in 3 ml of ethanol and a solution of 2 N hydrogen chloride in ethyl acetate was added until the pH was 2. After crystallization occured, the mixture was vacuum filtered and the product was crystallized from isopropanol to obtain 1.3 g of (7a-R,S-trans) 5-bromo-4,6,7,7a,8,9,10,11a-octahydro-8-propyl-[1,4]-oxazino-[2',3'-4,5]cyclohept[1,2,3-c,d]indole hydrochloride melting at ≃265° C.

Analysis: $C_{17}H_{22}BrClN_2O$; molecular weight = 385.75. Calculated: %C, 52.93; %H, 5.75; %Br, 20.72; %Cl, 9.19; %N, 7.26. Found: %C, 53.2; %H, 5.8; %Br, 21.2; %Cl, 8.5; %N, 7.3.

EXAMPLE 5

(7a-R,S-trans) 4,6,7,7a,8,9,10,11a-octahydro-4-methyl-8-propyl-[1,4]-oxazino-[2',3'-4,5]cyclohept[1,2,3-c,d]indole hydrochloride 16 1 mg of sodium were added to 35 ml of liquid ammonium and the mixture was stirred at −40° C. for 15 minutes. 20 mg of ferric nitrate were added to the mixture which was stirred at −40° C. for 20 minutes after which a solution of 1.2 g of the free base of Example 3 in 18 ml of tetrahydrofuran was added thereto rapidly. The mixture was stirred at −40° C. for 10 minutes and then 0.5 ml of methyl iodide were added thereto. The temperature was allowed to rise to room temperature and 150 ml of water were added to the mixture. The mixture was extracted with methylene chloride and the organic phase was washed with aqueous saturated sodium chloride solution, dried and evaporated to dryness to obtain 1.3 g of residue. The latter was dissolved in ether and the solution was treated with activated carbon and evaporated to dryness to obtain 1.25 g of (7a-R,S-trans) 4,6,7,7a,8,9,10,11a-octa-hydro-4-methyl-8-propyl-[1,4]-oxazino-[2',3'-4,5]-cyclohept[1,2,3-c,d]indole.

The 1.25 g of product was dissolved in 5 ml of ethyl acetate and a solution of hydrogen chloride in ethyl acetate was added to adjust the pH to 2. The mixture was vacuum filtered and the product was washed with ethyl acetate and with ether and was crystallized from a methanol-isopropanol mixture to obtain 1 g of (7a-R,S-trans) 4,6,7,7a,8,9,10,11a-octahydro-4-methyl-8-propyl-[1,4]-oxazino-[2',3'-4,5]cyclohept[1,2,3-c,d]indole hydrochloride melting at 240°–250° C.

Analysis: $C_{18}H_{25}ClN_2O$; molecular weight = 320.86. Calculated: %C, 67.38; %H, 7.85; %Cl, 11.05; %N 8.73. Found: %C, 67.5; %H, 7.9; %Cl, 11.0; %N 8.6.

Preparation A: R,S-trans 5-methylamino-3,4,5,6-tetrahydro-1H-cyclohept[c,d]indol-6-ol hydrochloride.

Step a: Ethyl R,S-trans-N-(6-hydroxy-3,4,5,6-tetrahydro-1H-cyclohept[c,d]indol-5-yl)-carbamate 2.6 ml of ethyl chloroformate were added with stirring at room temperature over 10 minutes to a mixture of 2.62 g of the acetate of Example 1, 40 ml of water, 52 ml of ethyl acetate and 2.62 g of potassium carbonate and the mixture was stirred for one hour and was evaporated to dryness under reduced pressure. The residue was diluted with a little ice water and the mixture was triturated at room temperature for 30 minutes and was vacuum filtered. The product was dried under reduced pressure at 60°–70° C. and was then added to methanol with stirring. The mixture was filtered and the filtrate was concentrated. Crystallization was induced and the mixture was iced for 3 hours and was filtered to obtain 1.45 g of ethyl R,S-trans-N-(6-hydroxy-3,4,5,6-tetrahydro-1H-cyclohept[c,d]indol-5-yl)-carbamate in the form of crystals melting at 190° C.

Step b: R,S-trans 5-methylamino-3,4,5,6-tetrahydro-1H-cyclohept[c,d]indol-6-ol hydrochloride A solution of 1.83 g of the product of Step A in 75 ml of dioxane were added over 20 minutes with stirring under an inert atmosphere at room temperature to a suspension of 3.6 g of aluminum hydride in 50 ml of tetrahydrofuran and the mixture was refluxed for 2 hours and was cooled, 50 ml of tetrahydrofuran containing 10% water were added over 30 minutes to the mixture which was then diluted with 50 ml of water and filtered. The filter was rinsed with ethyl acetate and sodium chloride was added to the filtrate. The decanted aqueous phase was extracted with ethyl acetate and the organic phase was washed with water, with aqueous saturated sodium chloride solution, dried over sodium sulfate and evaporated to dryness to obtain 2 g of raw R,S-trans 5-methylamino-3,4,5,6-tetrahydro-1H-cyclohept[c,d]indol-6-ol. The said product was dissolved in 3 ml of ethanol and 1.5 ml of 5 N hydrochloric acid in ethanol were added thereto dropwise. The mixture was iced for one hour and was filtered. The product was washed with ethanol and dried under reduced pressure at 70° C. to obtain 1.24 g of R,S-trans 5-methylamino-3,4,5,6-tetrahydro-1H-cyclohept[c,d]indol-6-ol hydrochloride melting at 224° C. with decomposition.

Analysis: $C_{13}H_{16}N_2O$, HCl; molecular weight = 252.7. Calculated: %C, 61.78; %H, 6.78; %N, 11.08; %Cl, 14.03. Found: %C, 61.8; %H, 6.7; %N, 11.1; %Cl, 13.9.

Preparation B: (RS-trans) 5-(1-methylethyl) amino 3,4,5,6-tetrahydro 1H-cyclohept/c,d/indol-6-ol.

Under agitation and in an inert atmosphere, 10.5 g of (RS-trans) 5-amino 3,4,5,6-tetrahydro 1H-cyclohept/c,- d/indol-6-ol acetate is put into suspension in 105 cm³ of methanol and 52.5 cm³ of acetone, cooled to about 0° C., and over 15 minutes 10.5 g of sodium cyanoborohydride is added. After agitating for 3 hours 30 minutes at about 0° C., filtering, rinsing with ethyl acetate, evaporating to dryness and chromatographing under pressure on a silica column (eluting with benzene-ethyl acetate-triethylamine 7-21), 6.32 g of crystals are recuperated. The crystals are redissolved in 6 cm³ of hot ethyl acetate; after allowing to cool, initiating crystallization at −15° to −20° C., leaving at this temperature for 1 hour 30 minutes, separating and drying under reduced pressure at ambient temperature, 4.03 g of white crystals are obtained which melt at 100° C.

Analysis: $C_{15}H_{20}N_2O = 244.338$. Calculated: C%, 73.74; H%, 8.25; N% 11.46. Found: C%, 73.5; H%, 8.3; N%, 11.4.

EXAMPLE 6

Tablets were prepared containing either 20 mg of (7a-R,S-trans) 8-methyl-4,6,7,7a,8,9,10,11a-octahydro-[1,4]-oxazino[2',3'-4,5]-cyclohept-[1,2,3-c,d]-indole hydrochloride or 10 mg of (7a-R,S-trans) 4,6,7,7a,8,9,10,11a-octahydro-8-propyl-[1,4]-oxazino [2',3'-4,5]cyclohept-[1,2,3-c,d]-indole hydrochloride and sufficient excipient of lactose, starch, talc and magnesium for a final weight of 100 mg.

PHARMACOLOGICAL STUDY

A. Rotation behavior after unilateral injury of nigrostriatal bundle

The unilateral lesion was effected with male rats weighing about 220 g by unilateral injection into nigrostriatal dopaminergic bundle of 8 μg of 6-hydroxydopamine in a solution of 2 μg per μl by the method of Ungerstedt [Acta. Physiol. Scand., Vol. 82 (1971), supp. 367, p. 69-93]. In the animals, the direct dopaminergic agonists such as apomorphine administered generally induces a rotating behavior in the contralateral direction to the injured side. The test compounds were administered more than 5 weeks after the lesion and the rats were placed in an automatic rotometer which determine the number of rotations effected by each animal in 2 directions.

The products of Examples 1, 2 and 3 were intraperitoneally administered and the product of Example 1 provoked 337±99 contralateral rotations at a dose of 5 mg/kg, product of Example 2 provoked 364±50 contralateral rotations at a dose of 1 mg/kg and the product of Example 3 provoked 657±205 contralateral rotations at a dose of 0.1 mg/kg.

B. Affinity for dopaminergic receptors

The striated bodies taken from the brains of 6 male rats weighing about 150 g were homogenized at one 20th (weight/volume) in 0.32 M sucrose and the homogenized mixture was centrifuged at 1000 g for 10 minutes at 0° C., the surnageant was centrifuged at 30,000 g for 15 minutes at 4° C. The culot was taken up in 25 ml of buffered Tris HCl 50 mM with a pH of 7.7 and the mixture was centrifuged at 30,000 g for 15 minutes at 4° C. The new culot was taken up in 50 ml of buffered Krebs Tris HCl with a pH of 7.3 and the suspension was preincubated at 37° C. for 10 minutes and was then incubated for 20 minutes in a water bath at 37° C. in the presence of spiroperidol $3_H$, alone or with an excess of haloperidol or with increasing units of the product being tested. The incubated suspensions were filtered with Whatman GF/C and the filters were washed 3 times with 5 ml of buffered Tris HCl 50 mM. The radioactivity of the filters was measured by liquid scintillation and the curve of percentage of fixation of spiroperidol $3_H$ as a function of concentration of test product was determined. The concentration of the test compound which inhibited the maximum fixation by 50% of spiroperidol $3_H$ is reported in Table I.

TABLE I

| Compound of Example | 50% inhibiting concentration in nm |
|---|---|
| 1 | 10,000 |
| 2 | 950 |
| 3 | 270 |

The results of Table I show that the products of Exampls 1,2 and 3 do fix dopaminergic receptors.

C. Hypobare anoxia study

Groups of 10 male mice weighing about 20 to 22 g were not fed for 5 hours and were placed in a hermetically sealed enclosure with a pressure of 90 mm Hg maintained by a pump to determine the time of their survival. The test products were orally administered 30 minutes before the test and the mice were observed for 2 minutes. The results of Table II show the increase of survival time expressed as a percentage of control animals.

TABLE II

| Product of Example | Dose in mg/kg | % of increase of survival time |
|---|---|---|
| 1 | 50 | 145 |
|   | 10 | 51 |
|   | 2 | 14 |
| 2 | 25 | 64 |
|   | 5 | 30 |
| 3 | 25 | 86 |
|   | 5 | 102 |
|   | 1 | 3 |

D. Antiulcerous activity

The technique used is described by Shay et al [Gastroenterology, Vol. 5 (1945), p. 43]. Ulcers were induced in the stomachs of rats by ligature of pylore. The animals were anesthesized with ether and a longitudinal incision of about 1 cm was made beneath the sternum, the glandular part of the stomach and the duodenum were taken out and a ligature was placed a few mm below the pylore. The muscular surface was left as it was and the skin was sutured by 2 clamps.

The animals received orally immediately after a dispersive or the test product in a volume of 0.5 ml/100 g and were kept without food or water until they were killed by carotidinal bleeding which was about 16 hours after treatment. Before removal of the stomach, a ligature was placed above the heart. The gastric liquid was collected to measure the pH and the stomach was then opened by a large curve, was rinsed with physiological serum and was spead out on millimetric paper for examination with a binocular lens. The gravity of the lesions was macroscopically evaluated on a scale of 0 to 4 for each stomach to determine for each group of rats the average intensity of ulcerations. The percent of protection with respect to a control group is reported in Table III.

TABLE III

| Product of Example | Dose in mg/kg | % protection against ulceration |
|---|---|---|
| 3 | 25 | 73 |
|   | 5 | 51 |

E. Acute toxicity

The $DL_0$ lethal dose of the different compounds after oral administration to mice was determined as the maximum dose which did not cause mortality and the results are in Table IV.

TABLE IV

| Product of Example | $DL_0$ in mg/kg |
|---|---|
| 1 | 200 |
| 2 | 100 |
| 3 | 100 |
| 4 | >1000 |
| 5 | 200 |

Various modifications of the products and processes of the invention may be made without departing from the spirit or scope thereof and it should be understood that the invention is intended to be limited only as defined in the appended claims.

We claim:

1. a compound selected from the group consisting of optically active isomers and racemic mixtures of cyclohept indoles of the formula

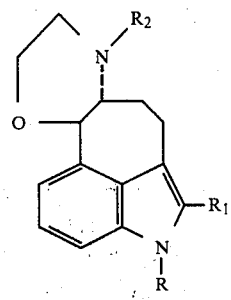

I wherein R is selected from the group consisting of hydrogen, alkyl of 1 to 5 carbon atoms and optionally substituted aralkyl of 7 to 12 carbon atoms, $R_1$ is selected from the group consisting of hydrogen, chlorine and bromine and $R_2$ is selected from the group consisting of hydrogen, alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and their non-toxic, pharmaceutically acceptable acid addition salts.

2. A compound of claim 1 wherein $R_2$ is selected from the group consisting of hydrogen, alkyl of 1 to 5 carbon atoms and cycloalkylalkyl of 4 to 7 carbon atoms and R is selected from the group consisting of hydrogen, methyl and benzyl.

3. A compound of claim 1 wherein $R_1$ is selected from the group consisting of hydrogen and bromine and $R_2$ is selected from the group consisting of hydrogen and alkyl of 1 to 5 carbon atoms.

4. A compound of claim 1 which is (7a-R,S-trans) 4,6,7,7a,8,9,10,11a-octahydro-[1,4]-oxazino[2',3'-4,5]-cyclohept[1,2,3-c,d]indole hydrochloride.

5. A compound of claim 1 which is (7a-R,S-trans) 8-methyl-4,6,7,7a,8,9,10,11a-octahydro-[1,4]-oxazino-[2',3'-4,5]-cyclohept[1,2,3-c,d]indole hydrochloride.

6. A compound of claim 1 which is (7a-R,S-trans) 8-propyl-4,6,7,7a,8,9,10,11a-octahydro-[1,4]-oxazino-[2',3'-4,5]-cyclohept[1,2,3-c,d]indole hydrochloride.

7. An antianoxic and dopaminergic agonist composition comprising an antianoxically and dopaminergic agonistically effective amount of at least one compound of claim 1 and a pharmaceutical carrier.

8. A composition of claim 7 wherein $R_2$ is selected from the group consisting of hydrogen, alkyl of 1 to 5 carbon atoms and cycloalkylalkyl of 4 to 7 carbon atoms and R is selected from the group consisting of hydrogen, methyl and benzyl.

9. A composition of claim 7 wherein $R_1$ is selected from the group consisting of hydrogen and bromine and $R_2$ is selected from the group consisting of hydrogen and alkyl of 1 to 5 carbon atoms.

10. A composition of claim 7 wherein the compound is (7a-R,S-trans) 4,6,7,7a,8,9,10,11a-octahydro-[1,4]-oxazino-[2',3'-4,5]-cyclohept[1,2,3-c,d]indole hydrochloride.

11. A composition of claim 7 wherein the compound is (7a-R,S-trans) 8-methyl-4,6,7,7a,8,9,10,11a-octahydro-[1,4]-oxazino-[2',3'-4,5]-cyclohept[1,2,3-c,d]indole hydrochloride.

12. A composition of claim 7 wherein the compound is (7a-R,S-trans) 8-propyl-4,6,7,7a,8,9,10,11a-octahydro-[1,4]-oxazino-[2',3'-4,5]-cyclohept[1,2,3-c,d]indole hydrochloride.

13. A method of inducing antianoxic and dopaminergic agonist activity in warm-blooded animals comprising administering to warm-blooded animals an amount of at least one compound of claim 1 sufficient to include antianoxic and dopaminergic agonist activity.

14. A method of claim 13 wherein $R_2$ is selected from the group consisting of hydrogen, alkyl of 1 to 5 carbon atoms and cycloalkylalkyl of 4 to 7 carbon atoms and R is selected from the grop consisting of hydrogen, methyl and benzyl.

15. A method of claim 13 wherein $R_1$ is selected from the group consisting of hydrogen and bromine and $R_2$ is selected from the group consisting of hydrogen and alkyl of 1 to 5 carbon atoms.

16. A method of claim 13 which is (7a-R,S-trans) 4,6,7,7a,8,9,10,11a-octahydro-[1,4]-oxazino-[2',3'-4,5]-cyclohept [1,2,3-c,d]indole hydrochloride.

17. A method of claim 13 which is (7a-R,S-trans) 8-methyl-4,6,7,7a,8,9,10,11a-octahydro-[1,4]-oxazino-[2',3'-4,5]-cyclohept[1,2,3-c,d]indole hydrochloride.

18. A method of claim 13 which is (7a-R,S-trans) 8-propyl-4,6,7,7a,8,9,10,11a-octahydro-[1,4]-oxazino-[2',3'-4,5]-cyclohept[1,2,3-c,d]indole hydrochloride.

* * * * *

UNITED STATES PATENT AND TRADEMARK OFFICE
CERTIFICATE OF CORRECTION

PATENT NO. : 4,313,944
DATED : February 2, 1982
INVENTOR(S) : LUCIEN NEDELEC ET AL.

It is certified that error appears in the above—identified patent and that said Letters Patent is hereby corrected as shown below:

Column 1, line 54: "cycloalky-" should read -- cycloalkyl- --.

line 55: "lalkyl" should read -- alkyl --.

Column 13, line 8: "7-21" should read -- 7-2-1 --.

Signed and Sealed this

First Day of June 1982

[SEAL]

Attest:

Attesting Officer

GERALD J. MOSSINGHOFF
Commissioner of Patents and Trademarks